United States Patent [19]

Wenzel

[11] Patent Number: 5,136,105
[45] Date of Patent: Aug. 4, 1992

[54] OXIDATION OF TERMINAL OLEFINS TO ALDEHYDES

[75] Inventor: Timothy T. Wenzel, Charleston, W. Va.

[73] Assignee: Union Carbide Chemicals & Plastics Technology Corporation, Danbury, Conn.

[21] Appl. No.: 676,439

[22] Filed: Mar. 28, 1991

[51] Int. Cl.$^5$ .............................................. C07C 45/34
[52] U.S. Cl. ...................................... 568/478; 568/476
[58] Field of Search ............................... 568/476, 478

[56] References Cited

PUBLICATIONS

Hosokawa et al, "Palladium (II)-catalyzed Acetalization of Terminal Olefins Bering Electron-withdrawing Substitutents with 1,3-and 1,2-Diols", Chem. Soc., Chem. Commun., 1983, pp. 848-849.

Hosokawa et al, "Catalysis of Pd(II)-Catalyzed Acetalization of Alkenes with Diols", Bull. Chem. Soc. Jpn., 63, 166-169 (1990) vol. 63, No. 1).

Ben L. Geringa, "Catalytic Oxidation of Alk-1-enes to Aldehydes", J. Chem. Soc., Chem. Commun., 1986, pp. 909-910.

*Primary Examiner*—Werren B. Lone
*Attorney, Agent, or Firm*—Sharon H. Hegedus

[57] ABSTRACT

A process for the oxidation of a compound having a terminal carbon-carbon double bond to produce the corresponding aldehyde is disclosed. In one embodiment, the process comprises contacting the compound with molecular oxygen in the presence of a Group VIII metal component initially substantially free of NO ligands and $NO_2$ ligands in an amount effective to promote the oxidation of the compound, a reoxidation component in an amount effective to reoxidize a reduced Group VIII metal component to the Group VIII metal component and at least one alcohol selected from secondary alcohols, tertiary alcohols and mixture thereof in an amount effective to increase the aldehyde selectivity of the oxidation. The contacting occurs at conditions effective to oxidize the compound and the form the corresponding aldehyde.

45 Claims, No Drawings

OXIDATION OF TERMINAL OLEFINS TO ALDEHYDES

BACKGROUND OF THE INVENTION

The present invention relates to processes for the oxidation of a compound having a terminal carbon-carbon double bond, for example, an alpha olefin, to produce the corresponding aldehyde. In particular, the invention relates to such processes in which the compound is contacted with molecular oxygen in the presence of a Group VIII metal component.

Palladium chloride has been known since 1894 to stoichiometrically oxidize ethylene to acetaldehyde in the presence of water. Co-catalysts, such as $CuCl_2$, could reoxidize the elemental palladium, Pd(O), that was formed back to the active palladium, Pd(II), have been added to provide enhanced results.

Palladium-based oxidation reactions have been extended to higher olefins. Under most conditions, only methyl ketones are formed from alpha olefins. However, aldehydes have been observed in the stoichiometric reactions with palladium salts.

Aldehydes produced from compounds having terminal carbon-carbon double bonds are useful for many purposes, for example, in pharmaceuticals, flavors and fragrances. In addition, such aldehydes can be employed as precursors or intermediates for other valuable products. For example, 3-acetoxypropionaldehyde may be used as a precursor for 1,3-propanediol.

It would be advantageous to provide effective and efficient processes for the production of aldehydes from compounds having a terminal carbon-carbon double bond, such as alpha olefins.

Feringa U.S. Pat. No. 4,661,642 discloses a process for the oxidation of alpha olefins to the corresponding aldehyde and ketone. The process involves contacting the alpha olefin and molecular oxygen in the presence of a solution of a Group VIII metal complex containing at least one $NO_2$ or NO ligand, a divalent copper salt and a tertiary alcohol as solvent. The results presented in this patent indicate that 1-decene can be oxygenated to a 60:40 (molar) mixture of aldehyde to ketone after 1.1 hours, although the ratio dropped to 18:82 after 2.1 hours. The $NO_2$ or NO ligand-containing complex is made using stoichiometric silver, thus increasing the cost of the catalyst. In addition, only about 7 turnovers, that is, mols of aldehyde plus ketone per mol of palladium, were achieved before the catalysts described in this patent became ineffective. Processes which provide increased selectivities to and yields of aldehydes and/or increased numbers of turnovers are desirable from effectiveness and efficiency standpoints.

SUMMARY OF THE INVENTION

New processes for the oxidation of a compound having a terminal carbon-carbon double bond to produce the corresponding aldehyde have been discovered. These processes provide large yields of the desired aldehydes very effectively and efficiently with a given quantity of catalyst. In addition, one or more other components may be included in the reaction mixture to provide further process enhancements. Moreover, the catalyst systems employed in the present processes may be derived with little or no complex processing, without the need for relatively expensive silver, and may be used in a substantially homogeneous combination with the reactants or in a heterogeneous catalyst/reactant system.

In one broad aspect, the present processes comprise contacting at least one compound having a terminal carbon-carbon double bond with molecular oxygen in the presence of at least one Group VIII metal component initially substantially free of $NO_2$ ligands and NO ligands in an amount effective to promote the oxidation of the compound. This contacting step further occurs in the presence of at least one alcohol selected from secondary alcohols, tertiary alcohols and mixtures thereof. The alcohol is present in an amount effective to increase the aldehyde selectivity of the oxidation relative to conducting the contacting in the presence of a corresponding primary alcohol. This contacting occurs at conditions effective to oxidize the compound and form the corresponding aldehyde.

In one embodiment, the contacting takes place in the presence of at least one reoxidation component in an amount effective to reoxidize a reduced Group VIII metal component to the Group VIII metal component used to promote the oxidation of the compound.

In a further aspect of the present invention, the contacting occurs in the presence of at least one copper component in an amount effective to facilitate the oxidation of the compound. In a particularly useful embodiment, at the time of the initial contacting of the compound and molecular oxygen in the presence of the Group VIII metal component, at least a portion, preferably a major portion, of the copper in the copper component is monovalent copper. The monovalent copper has been found to be effective to increase the overall rate of oxidation of the compound, for example, by reducing the length of or by eliminating the induction period which often occurs when divalent copper is used, for example, in combination with Group VIII metal chlorides.

DETAILED DESCRIPTION OF THE INVENTION

The present invention is directed to processes for the oxidation of a compound having a terminal carbon-carbon double bond to produce the corresponding aldehyde. The present processes involve contacting this compound with molecular oxygen in the presence of a Group VIII metal component in an amount effective to promote the oxidation of the compound and at least one alcohol selected from secondary alcohols, tertiary alcohols and mixtures thereof in an amount effective to increase the aldehyde selectivity of the oxidation relative to conducting the contacting in the presence of a corresponding primary alcohol in place of the at least one selected alcohol. The contacting is conducted at conditions effective to oxidize the compound and form the corresponding aldehyde.

Any suitable compound or mixture of compounds having a terminal carbon-carbon double bond may be oxidized in accordance with the present invention. Although the compound may include more than one carbon-carbon double bond, it is preferred that the compound have only a single carbon-carbon double bond, a terminal carbon-carbon double bond. The compound preferably contains 2 or 3 to about 30, more preferably 2 to 3 to about 18, carbon atoms per molecule. The compound may include one or more aliphatic portions, substituted aliphatic portions, cycloaliphatic portions, substituted cycloaliphatic portions, aromatic portions, substituted aromatic portions and mixtures and combinations thereof. The substituted groups or portions noted herein are the corresponding hydrocarbyl group or portion substituted with one or more substituent groups including elements such as oxygen, nitrogen, carbon, hydrogen, halogen, sulfur, phosphorus and the like and mixtures and combinations thereof. Such substituent groups may be bonded to one, two or more carbon atoms in the compound. Examples of suitable compounds include aliphatic olefins with a terminal carbon-carbon double bond, such as linear 1-alkenes, non-linear 1-alkenes and the like; aromatic olefins, such as styrene and the like; and substituted olefins such as allyl alcohol, allyl acetate and the like. Allyl acetate is a particularly useful component, at least in part because its corresponding aldehyde, i.e., 3-acetoxyaldehyde, is a potentially attractive precursor, for example, in the production of 1,3-propanediol.

The Group VIII metal component useful in the present invention to promote the oxidation of the compound is selected from any suitable such component or mixture of such components effective to promote such oxidation. The Group VIII metal component, or at least the source of the Group VIII metal component (that is the Group VIII metal-containing entity which is introduced into the reaction zone where the oxidation reaction occurs) may be in the form of elemental metal, metal salts and/or metal complexes. Preferably, the Group VIII metal in the Group VIII metal component used to promote the oxidation of the compound has an oxidation state greater than zero, for example a +2 or +3 oxidation state. Although the promoting Group VIII metal component may be present, at least in part, in a solid phase (heterogenous catalytic reaction), this component is preferably substantially soluble in the alcohol present during the reaction contacting at contacting conditions (homogenous catalytic reaction).

Examples of useful Group VIII metal components included rhodium components, palladium components, platinum components, ruthenium components and mixtures thereof. Particularly useful Group VIII metal components are those selected from palladium containing components, such as elemental palladium, palladium-containing compounds, palladium-containing complexes and the like and mixtures thereof. Palladium-containing complexes, especially palladium (II) complexes, provide very good results. Specific examples of useful Group VIII metal components, or at least sources of such Group VIII metal components, include halides, such as chlorides, iodides and bromides; oxides; sulfates; phosphates; sulfonates; carbonates; carboxylates; complexes with ligands such as acetylacetonate ligands, carbonyl ligands, ligands derived from one or more nitriles, ligands derived from heterocyclic aromatic nitrogen compounds (such as, for example, pyridine, bipyridine, terpyridines, phenathroline, porphyrins, phthalocyanins, N,N-bissalicylidene-0-phenylendiamino and the like and mixtures thereof); and the like and mixtures thereof. The ligands included in the Group VIII metal component are preferably substantially non-oxidizable, that is, they are not susceptible to substantial oxidation at the reaction or contacting conditions. Particularly useful Group VIII metal complexes include one or more ligands derived from one or more nitriles. The ligand producing compounds are preferably present in an amount in excess of that needed to form the desired Group VIII metal-containing complex.

A particularly useful Group VIII metal-containing complex is $(CH_3CN)_2PdCl_2$.

Although it is preferred that the Group VIII metal component be present in solution in the alcoholic reaction mixture, the Group VIII metal component may be deposited or otherwise associated with a solid support material, e.g., to form a heterogenous catalyst. Any suitable support material may be employed, provided that it does not unduly interfere with the oxidation reaction or overall process. Examples of useful support materials include carbon, such as graphite and the like; inorganic oxides, such as silica, alumina, silica alumina and the like; clays and the like and mixtures thereof. The Group VIII metal component, or source (precursor) thereof, can be deposited or otherwise associated with the support material using conventional and well known heterogenous catalyst preparation techniques, such as impregnation, precipitation, co-precipitation and the like. One or more additional processing steps may be employed to prepare the final, supported Group VIII metal component-containing catalyst.

The Group VIII metal component may be produced separately and introduced as such into the reaction zone and/or it may be produced in situ at the contacting conditions.

The amount of Group VIII metal component is such as to promote the oxidation of the compound and may vary over a wide range. Suitable amounts include those in the range of about 0.01 mmol (millimol) to about 100 mmol or more, preferably in the range of about 0.1 mmol to about 10 mmol, per mol of the compound to be oxidized.

In certain embodiments of the present invention, it is important that the Group VIII metal component be substantially free of NO and $NO_2$ ligands, particularly during the initial stage or stages of the reaction contacting. For example, in certain embodiments, at the time of the initial contacting at reaction conditions it is preferred that the Group VIII metal component be substantially free of NO and $NO_2$ ligands. More preferably, the Group VIII metal component introduced into the reaction zone is substantially free of $NO_2$ and NO ligands. Such ligands have been found to adversely affect both the rate of oxidation and the overall yield of the desired aldehyde. For example, the use of Group VIII metal components containing such ligands has been found to result in a reduced number of turnovers (or reduced turnover numbers) relative to employing a Group VIII metal component substantially free of such ligands. Without wishing to limit the present invention to any particular theory of operation, it is believed that Group VIII metal components containing $NO_2$ and/or NO ligands interact with the compound to be oxidized in a manner which does not yield the desired aldehyde. Moreover, the resulting reaction mixture is less active or effective in producing the desired aldehyde relative to a reaction mixture in which the Group VIII metal component is initially substantially free of $NO_2$ and NO ligands.

The present contacting occurs in the presence of at least one alcohol selected from secondary alcohols and tertiary alcohols and mixtures thereof in an amount effective to increase the aldehyde selectivity of the oxidation reaction relative to conducting the reaction contacting in the presence of a corresponding primary alcohol in place of the at least one alcohol. In many instances, the alcohol is present in an amount effective to act as a solvent for one or more other components of the reaction mixture at reaction conditions. The alcohol is preferably present in an amount at least equal to the molar concentration of the compound to be oxidized. The presently useful alcohols may be considered "branch chained" or "sterically hindered" alcohols. Although the presently useful alcohols may include more than one hydroxyl group, the preferred alcohols include a single hydroxyl group. In addition, the alcohols are preferably aliphatic.

The presently useful secondary alcohols include at least one carbon atom which is directly bonded to a hydroxyl group, to a hydrogen atom and to two other entities, preferably to two carbon atoms, other than hydrogen atoms. The presently useful tertiary alcohols include at least one carbon atom which is directly bonded to a hydroxyl group and to three other entities, preferably to three carbon atoms, other than hydrogen atoms. Although the presently useful alcohols can include one or more substantially non-interfering substituent groups, derived from one or more of the elements noted previously with regard to substituent groups, it is preferred that the alcohols, except for the hydroxyl group or groups, be substantially hydrocarbon in nature.

The presently useful alcohols may include as few as 3 (for secondary alcohols) or 4 (for tertiary alcohols) carbon atoms per molecule. Such alcohols preferably contain up to about 12, more preferably up to about 9, carbon atoms per molecule. Specific examples of useful alcohols include isopropanol, sec-butanol, tertiary butyl alcohol, 2-methyl-2-pentanol, 3-methyl-2-pentanol, 2-methyl-2-hexanol, 3-methyl-2-hexanol, 2-ethyl-2-hexanol, 3-ethyl-2-hexanol and the like and mixtures thereof.

Particularly useful are tertiary alcohols, especially tertiary butyl alcohol.

As used herein, the term "corresponding primary alcohol" refers to the linear primary alcohol having the same number of carbon atoms per molecule as the secondary or tertiary alcohol being used in the present reaction contacting.

In one embodiment of the present invention, a reoxidation component is employed in an amount effective to reoxidize a reduced Group VIII metal component to the Group VIII metal component employed to promote the oxidation. The reoxidation of the reduced Group VIII metal component forms a reduced reoxidation component which is preferably oxidized, e.g., by molecular oxygen, to the reoxidation component at the contacting conditions. This reduction/oxidation cycling (or redox cycling) provides a very convenient and effective way to maintain the Group VIII metal component in the active oxidation state, thereby prolonging the effective life of the Group VIII metal component. The amount of the reoxidation component used may vary over a wide range depending, for example, on the specific reoxidation component and the specific Group VIII metal component being employed. Care should be exercised to avoid using excessive amounts of reoxidation components, that is, amounts which cause significant or substantial compound oxidation to products other than the desired aldehyde. Determining what amount of any given reoxidation component is excessive can be accomplished by running a series of experiments at varying concentrations of the specific reoxidation component. In many instances, it is preferred to use a reoxidation component in an amount in the range of about 0.1 mmol to about 100 mmol, more preferably about 2 mmol to about 10 mmol, of the reoxidation component per mmol of the Group VIII metal component present. The reoxidation component is preferably soluble in the alcohol of the reaction mixture at contacting conditions.

In one embodiment, the reoxidation component comprises a component of a metal which is redox active at the contacting conditions, that is, a metal which can be both reduced and oxidized or is redox cyclable at the contacting conditions. Any suitable redox active metal component may be employed. Such metal components preferably comprise a metal selected from copper, iron, cobalt, chromium, molybdenum, tungsten, vanadium, bismuth, manganese and mixtures thereof. A particularly useful example of such a metal is copper.

In one useful embodiment, the present contacting takes place in the presence of a copper component in an amount effective to facilitate the oxidation of the compound. This copper component, which may be introduced into the reaction or contacting zone as either a divalent copper component, a monovalent copper component or mixtures thereof, may act to reoxidize a reduced Group VIII metal component to the Group VIII metal component which promotes the oxidation of the compound.

The redox active metal or metals may be introduced or included in the reaction contacting in any suitable form, for example, as an elemental metal, a compound and/or a complex. Specific examples of useful redox active metal components, or at least sources of such redox active metal components, include halides, oxides, sulfates, phosphates, sulfonates, carbonates, carboxylates, redox active complexes of such metals and the like and mixtures thereof. Halides, and in particular chlorides, are very useful redox active metal components.

The reoxidation component may comprise one or more polyoxoanions which are capable of reoxidizing the reduced Group VIII metal component in the presence of molecular oxygen at reaction conditions. Without wishing to limit the invention to any particular theory of operation, it is believed that the useful polyoxoanions reoxidize the reduced Group VIII metal component in a manner substantially similar to that in which the redox active metal components function as reoxidation components. Examples of suitable polyoxoanions include $K_9PMo_6V_6O_{40}$, $H_3PMo_6W_6O_{40}$ and the like and mixtures thereof.

The reoxidation component may comprise one or more organic components, for example, such components which are redox active at the contacting conditions. Particularly useful are organic components which include at least one nitrite group, i.e., —ONO, which is reducible at the contacting conditions. Particularly useful organic nitrites are selected from compounds having the following formula:

R(—ONO)ₐ and mixtures thereof, wherein R is selected from hydrocarbyl radicals and substituted hydrocarbyl radicals, preferably containing 1 to about 10 carbon atoms, and a is an integer in the range of 1 to about 10, preferably 1. The R group may be any suitable hydrocarbyl or substituted hydrocarbyl group provided that the organic nitrite functions as described herein and does not unduly interfere with the present oxidation or the overall process. The R group may include one or more substituents, for example, including one or more of the elements noted previously for inclusion in substituent groups. Preferably, R is chosen so as to be substantially non-oxidizable at the contacting conditions. Particularly useful organic nitrite components include those in which R is alkyl, for example, methyl, ethyl, propyl, butyl, hexyl, octyl, decyl and the like. An especially useful organic nitrite component is tertiary butyl nitrite, $(CH_3)_3—C—ONO$.

The above-noted organic nitrite components may advantageously be present during the reaction contacting in an amount effective to facilitate the oxidation of the compound, even in the presence of another effective reoxidation component. Such organic nitrite component or components are preferably present during the reaction contacting in an amount effective to increase the yield of the desired aldehyde and/or corresponding ketone relative to a similar reaction contacting in the absence of such organic nitrite component or components. Such facilitating or yield increasing amounts of organic nitrite components may be as described previously with regard to the use of such nitrite components as reoxidation components. The organic nitrite components may function both as reoxidation components and as oxidation facilitating components in a single reaction contacting. The organic nitrite components are very useful when employed in conjunction with a copper component, particularly if at least a portion of the copper component is monovalent copper.

In one embodiment, the present contacting takes place in the presence of monovalent copper in an amount effective to increase the yield of the corresponding aldehyde and the corresponding ketone from the oxidation. The presence of monovalent copper, in particular at the time of the initial contacting of the compound to be oxidized and molecular oxygen in the presence of the Group VIII metal component, may reduce the length of, or even eliminate, the prolonged induction period which is often experienced if the copper is present as divalent copper. Thus, although divalent copper is useful to reoxidize reduced Group VIII metal component to the active or promoting Group VIII metal component, monovalent copper acts to enhance the yield of the desired aldehyde product. In order to take good advantage of this feature, it is preferred that a major amount, and more preferably substantially all, of the copper present at the time of the initial contacting of the compound and molecular oxygen in the presence of the Group VIII metal component be monovalent copper.

The monovalent copper may be included in the contacting in any suitable manner, for example, such as the source or precursor of redox active metal reoxidation component. Halides, and in particular cuprous chloride, CuCl, are preferred. The amount of monovalent copper present at the time of the initial contacting of the compound and molecular oxygen in the presence of the Group VIII metal component is in the range of about 0.1 mmols to about 100 mmols, more preferably about 2 mmols to about 10 mmols, per mmol of Group VIII metal component.

In one useful embodiment, the present reaction contacting, at least initially, takes place in the presence of a divalent copper component and at least one monovalent copper yielding component in an amount effective to do at least one of the following: (a) reduce (chemically reduce) at least a portion of the divalent copper to monovalent copper at the contacting conditions; and (b) inhibit the oxidation of monovalent copper to divalent copper at the contacting conditions. This monovalent copper yielding component is preferably substantially free of the Group VIII metal being used in the contacting, although if the Group VIII metal is initially (at the time of the initial contacting of the compound to be oxidized and molecular oxygen in the presence of the Group VIII metal) present in the zero (0) oxidation state, this Group VIII metal (0) component can act as at least a portion of the monovalent copper yielding component. Examples of useful monovalent copper yielding components include basic components, copper reducing components and mixtures thereof. The monovalent copper yielding component or components should be selected so as to have no undue detrimental effect on the overall oxidation process or the product or products being produced.

Examples of basic components which may be utilized as monovalent copper yielding components include alkali metal hydroxides and basic salts, such as lithium hydroxide, sodium hydroxide, sodium acetate, potassium hydroxide and the like; alkaline earth metal hydroxides and basic salts, such as magnesium hydroxide, magnesium acetate, calcium hydroxide and the like; amines, such as triethylamine and the like; other basic components and the like and mixtures thereof. Examples of copper reducing components which may be utilized as monovalent copper yielding components include elemental metals, such as lithium, sodium, palladium, silver, mercury and the like; metal hydrides, such as $LiAlH_4$, $NaH$, $NaBH_4$, $CaH_4$ and the like; organic reducing agents, such as 2,6-di-t-butyl-p-cresol and the like; other reducing agents and the like.

The amount of monovalent copper yielding component initially included in the reaction contacting is preferably sufficient to produce or maintain at least about 5% of the total copper present as monovalent copper.

The contacting preferably occurs in the presence of at least one halide component in an amount effective to enhance at least one of the rate of oxidation and the aldehyde selectivity of the oxidation. This halide component is more preferably selected from chloride components and mixtures thereof. Useful examples of halide components include alkali metal halides, such as sodium chloride, lithium chloride, cesium chloride and the like; alkaline earth metal halides, such as magnesium chloride, calcium chloride and the like; quaternary ammonium halides, such as tetraalkyl ammonium chlorides containing about 4 to about 40 carbon atoms per molecule, e.g., methyl trioctyl ammonium chloride, and mixtures thereof. The halide component or components is preferably soluble in the alcohol of the reaction mixture at contacting conditions.

The halide component or components are preferably present in an amount in the range of about 0.1 mmol to about 100 mmol, more preferably about 2 mmol to about 10 mmol, of halide per mmol of Group VIII metal component.

It is often important to achieve the desired aldehyde product to inhibit the isomerization of the compound being oxidized, for example, to a compound having a carbon-carbon double bond which is not terminal. Thus, in one embodiment, the present invention provides for the contacting to occur in the presence of an inhibitor component in an amount effective to inhibit the isomerization of the compound at the contacting conditions, relative to conducting such contacting in the absence of the inhibitor component. The amount of inhibitor component present depends, for example, on the specific inhibitor component and compound to be oxidized being employed. In many instances, the inhibitor component is present in an amount in the range of about 0.1 mmol to about 100 mmol or more, more particularly about 2 mmol to about 10 mmol, per mmol of Group VIII metal component. A particularly useful inhibitor component comprises divalent copper component, such as that useful as a reoxidation component.

The inclusion/exclusion of water in the reaction contacting step may be used to provide one or more effects. For example, the contacting can be made to occur in the presence of water in an amount effective to perform at least one of the following: increase the rate of the oxidation, and inhibit the isomerization of the compound to be oxidized at the contacting conditions. To achieve one or more of these effects, water is preferably present in an amount 0.1 mol to about 40 mols of water per mol of Group VIII metal component present in the contacting. The contacting may occur from the substantial absence of water. This embodiment has been found to provide increased selectivity toward the desired corresponding aldehyde.

In one embodiment, the present process involves conducting the present contacting in the presence of a nitrile component, which is preferably substantially non-oxidizable at the contacting conditions. At least a portion of the nitrile component may act to form a ligand in the Group VIII metal component if the Group VIII metal component is present as a complex. Although the nitrile component or components may include electron withdrawing substituents and/or election donating substituents, electron withdrawing substituents are preferred since such nitrile components tend to provide higher yields of oxidized products, e.g., increase the rate of oxidation. Care should be exercised in selecting the nitrile component to be employed and the amount of the nitrile component to be employed. Some nitriles have been found to be poisons to the oxidation reaction, while relatively high concentrations of certain nitriles may increase the overall yield of oxidation products but disadvantageously reduce the aldehyde to ketone ratio. The effect of any particular nitrile and its concentration on the present process can be easily determined by running a series of experiments with varying concentrations of the nitrile in question.

The amount of nitrile component employed varies depending, for example, on the specific nitrile, Group VIII metal component and/or compound to be oxidized to be employed. For example, the amount of nitrile component may be in the range of about 0.1 mols or less to about 10 mols or more per mol of Group VIII metal component. In one embodiment, it is preferred that there be a molar excess of $-C\equiv N$ groups relative to the number of mols of Group VIII metal component present.

Many nitriles are useful in the present invention. Examples of useful nitrile components include 4-nitrobenzonitrile, 5-oxo-hexanenitrile, pentafluorobenzonitrile, isophorone nitrile, pivalonitrile, benzonitrile, 4-fluorobenzonitrile, fluoroacetonitrile, acetonitrile, isobutyronitrile, 2,5-dimethylbenzonitrile, polyacrylonitrile, 2,6-difluorobenzonitrile, para-nitrobenzonitrile and mixtures thereof. A particularly useful group of nitriles is selected from acetonitrile, benzonitrile, para-nitrobenzonitrile, 5-oxo-hexanenitrile and mixtures thereof. Especially useful nitrile compounds include para-nitrobenzonitrile, 5-oxo-hexanenitrile and mixtures thereof.

The molecular oxygen pressure employed during the contacting may be in the range of about atmospheric or less to about 200 psig or higher, more preferably about 20 to about 150 psig.

The contacting temperature may vary provided that at least one aldehyde is formed. Increasing temperature provides increased reaction rates. However, increasing temperatures may have an adverse effect on selectivity. Thus, the temperature is preferably chosen to achieve both acceptable reaction rates and acceptable selectivities. Preferred temperatures are in the range of about 0° C. to about 150° C., more preferably about 30° C. to about 80° C.

The reaction contacting may occur in any suitable manner, such as batch, semi-batch or continuous. In one embodiment, the compound to be oxidized is introduced into the reaction mixture including the Group VIII metal component at reaction conditions over a period of time, for example, on the order of about 10 minutes to about 5 hours or more. This "slow addition" feature has been found to provide increased aldehyde yields relative to a batch-wise addition of the compound at the start of the contacting period.

The contacting is conducted for a period of time sufficiently long to achieve the desired reaction, aldehyde formation. Such contacting time may be in the range of about 1 minute or less to about 10 hours or more.

After the reaction contacting, the product aldehyde is recovered from the reaction (product) mixture, for example, using conventional product recovery techniques, such as distillation, extraction, filtration and the like. One or more of the components separated from the product aldehyde can be reprocessed and/or recycled to the contacting zone for use in producing additional aldehyde.

The following non-limiting examples illustrate certain aspects of the invention.

Unless otherwise stated, oxidation reactions at greater than one (1) atmosphere molecular oxygen (O2) are run by charging all components except the olefin substrate to a Fischer Porter tube that contains a stir bar. The tube is capped with a septum and the mixture is stirred for one (1) hour at room temperature. The olefin substrate is then added and an initial sample removed for GC analysis. The tube is connected to a Fischer Porter manifold, purged with oxygen by three pressure/vent cycles to 80 psi oxygen, and immersed in an oil bath equilibrated to the desired temperature. Samples are occasionally withdrawn for GC analysis.

EXAMPLE 1

The following reaction mixture is subjected to 40 psi molecular oxygen at 60° C.:

0.25 mmol of $(CH_2CN)_2PdCl_2$
0.51 mmol of CuCl
1.0 mmol of $CuCl_2$
0.49 mmol of LiCl
7.1 mmol of 1-octene
5 ml of t-butyl alcohol Results of this reaction at 3 hours reaction time are as follows:

| | |
|---|---|
| Yield of octanaldehyde[1] | 12% |
| Yield of 2-octanone[1] | 26% |
| Selectivity to octanaldehyde[2] | 31% |

-continued

| Turnover number[3] | 10.8 |
|---|---|

[1] Based on 1-octene charged
[2] (mols of octanaldehyde over mols of octanaldehyde plus mols of octanone) × 100.
[3] Mols of octanaldehyde plus mols of octanone per mol of Pd.

EXAMPLE 2

The following reaction mixture is subjected to 40 psi molecular oxygen at 60° C.:

0.25 mmol of $(CH_3CN)_2PdCl_2$
1.5 mmol of $CuCl_2$
0.5 mmol of LiOH
7.2 mmol of 1-octene
5 ml of t-butyl alcohol Results of this reaction at 3 hours reaction time are as follows:

| Yield of octanaldehyde[1] | 14% |
|---|---|
| Yield of 2-octanone[1] | 39% |
| Selectivity to octanaldehyde[2] | 27% |
| Turnover number[3] | 15 |

[1] Based on 1-octene charged
[2] (mols of octanaldehyde over mols of octanaldehyde plus mols of octanone) × 100.
[3] Mols of octanaldehyde plus mols of octanone per mol of Pd.

The results obtained in Examples 1 and 2 are in contrast to the results reported in Feringa U.S. Pat. No. 4,661,642, which involved oxidizing 1-decene using a $(CH_3CN)_2PdClNO_2CuCl_2$ system in t-butyl alcohol. The results in this Feringa patent indicate that 1-decene was oxygenated to a 60:40 (molar) mixture of aldehyde to ketone after 1.1 hour, although this ratio dropped to 18:82 after 2.1 hours. Also, only about 7 turnovers were achieved before the catalyst became ineffective. Thus, the present system, as exemplified in Examples 1 and 2, provides an increased overall selectivity and yield of aldehyde, as well as a larger turnover number relative to using a palladium catalyst including $NO_2$ ligands.

In addition, Example 2 demonstrates that the inclusion of a basic component, such a LiOH, which inhibits the oxidation of monovalent copper is advantageous. Thus, the presence of monovalent copper at the time of the initial contacting of the compound to be oxidized, molecular oxygen and the Group VIII metal component, and/or the presence of divalent copper and a component capable of inhibiting the oxidation of monovalent copper at reaction conditions is useful in that monovalent copper reduces the length of, or eliminates, the induction period and/or increases the yield of desired aldehyde product.

EXAMPLES 3 TO 8

A series of six (6) 1-octene oxidation reactions are conducted at 60° C. Each of the reactions is conducted at 80 psi molecular oxygen. The palladium (Pd) species used is $(CH_3CN)_2PdCl_2$, and each reaction takes place in 5 ml of t-butyl alcohol.

Results of these reactions, as well as the results of Examples 1 and 2, are as follows:

| | mmol | | | | | at 5 hr reaction time | |
|---|---|---|---|---|---|---|---|
| Example | 1-octene | Pd | $CuCl_2$ | CuCl | LiCl | turnover[1] number | % aldehyde[2] |
| 3 | 6.2 | 0.26 | 2.0 | — | — | 0.17 | 41 |
| 4 | 7.5 | 0.26 | 2.0 | 0.52 | — | 6.5 | 25 |
| 5[3][4] | 7.0 | 0.26 | 2.0 | — | — | 15.4 | 15 |
| 6[3][5] | 6.2 | 0.26 | 2.0 | — | — | 8.8 | 26 |
| 7 | 7.2 | 0.26 | 2.0 | 0.52 | 0.53 | 21.0 | 16 |
| 8 | 5.9 | 0.26 | 1.0 | 0.51 | 0.54 | 21.1 | 16 |
| 1 | 7.1 | 0.25 | 1.0 | 0.51 | 0.49 | 10.8[6] | 31[6] |
| 2[7] | 7.2 | 0.25 | 1.5 | — | — | 15[6] | 27[6] |

[1] Mols of octanaldehyde plus mols of octanone per mol of Pd.
[2] (mols of octanaldehyde over mols of octanaldehyde plus mols of actanone) × 100.
[3] Add 0.5 ml of $CH_3CN$
[4] Add 0.2 mmol of $NaBH_4$
[5] Add 1.0 mmol 2,6-di-t-butyl-p-cresol
[6] At 3 hours reaction time
[7] Add 0.5 mmol of LiOH These results indicate that the relatively simple combination of $(CH_3CN)_2PdCl_2$ and $CuCl_2$ in t-butyl alcohol oxidizes 1-octene to a mixture of the aldehyde and ketone, but the rates are very slow due to a long induction period (of more than 5 hours in Example 3). The addition of CuCl, Example 4, eliminates this induction period. Further, the addition of a monovalent copper yielding component, such as $NaBH_4$, Example 5, 2,6-di-t-butyl-p-cresol, Example 6, or LiOH, Example 2, also reduces or eliminates the induction period and increases the overall aldehyde yield (turnover number). Although monovalent copper is useful, alkali metal halides, such as NaCl (Example 5) and LiCl (Examples 1, 2, 7, and 8) are also useful.

EXAMPLE 9

A 1-octene oxidation reaction is conducted in 5 ml of t-butyl alcohol at 60° C. and 40 psi molecular oxygen. This reaction mixture includes 0.25 mmol of $(CH_3CN)_2PdCl_2$ and 2.0 mmol of $CuCl_2$. The reaction mixture includes no CuCl.

Results of this test, along with corresponding results from the Example 1 reaction, are as follows:

| Reaction time, hr. | Example 9 | Example 1 |
|---|---|---|
| Turnover Number[1] | | |
| 0.5 | 0.3 | 2.2 |
| 1.0 | 1.3 | 3.6 |
| 1.5 | 3.3 | 5.3 |
| 2.0 | 5.4 | 7.1 |
| 2.5 | 8.0 | 8.9 |
| 3.0 | 10.7 | 10.8 |
| Aldehyde Selectivity[2], % | | |
| 0.5 | 57 | 30 |
| 1.0 | 48 | 34 |
| 1.5 | 39 | 33 |
| 2.0 | 35 | 32 |
| 2.5 | 31 | 31 |

-continued

| Reaction time, hr. | Example 9 | Example 1 |
|---|---|---|
| 3.0 | 28 | 31 |

(1) Mols of octanaldehyde plus mols of octanone per mol of Pd.
(2) (mols of octanaldehyde over mols of octanaldehyde plus mols of octanone) × 100.

The difference in turnover number in Example 9 and 1 is an indication of the induction period which is present in Example 10 (without CuCl) and is not present in Example 1 (with CuCl). The selectivity to aldehyde is more stable with CuCl (Example 1) than without CuCl (Example 9).

EXAMPLES 10 AND 11

Example 1 is repeated twice except that propylene (Example 10) and 1-butene (Example 11) is used in place of 1-octene, and the molecular oxygen pressure is 80 psi. The percent aldehyde in each case is similar to that found with 1-octene (about 16% aldehyde after 3 hours), although it decreases somewhat with time.

EXAMPLE 12

Example 1 was repeated except that allyl alcohol is used in place of 1-octene, and the molecular oxygen pressure is 80 psi. Complete conversion occurs within one (1) hour. The two major products are 3-t-butoxypropionaldehyde and t-butoxyacetone in about a 1:2 molar ratio. It appears that exchange of t-butyl alcohol with the hydroxy group occurred very quickly, followed by oxygenation of the resulting t-butoxy allyl ether.

EXAMPLE 13

Example 12 was repeated except that allyl acetate is used in place of allyl alcohol. Complete conversion is achieved in about three (3) hours. The major products are 3-acetoxypropionaldehyde and acetoxyacetone in about a 4:1 molar ratio. The rate of aldehyde formation remains fairly constant during the reaction, suggesting that there is little aldehyde decomposition. Other products include 3-t-butoxypropionaldehyde, t-butoxyacetone and 2(or 3) t-butoxypropyl (or propenyl) acetate.

EXAMPLE 14

Example 13 is repeated except that the $CuCl_2$ is omitted. A 55% selectivity for aldehyde from allyl acetate (including acetate and t-butoxy ethers) is achieved, with much less t-butoxy ether formation than in Example 13. Furthermore, the acetoxypropionaldehyde yield does not diminish during the reaction nearly as fast as in Example 13. Little of the apparent t-butoxypropyl (or propenyl) acetate product is formed. Some 3-t-butoxyacrolein is formed.

EXAMPLE 15

Example 14 is repeated except that acrolein is used in place of alkyl acetate. The resulting products include 3-t-butoxyacrolein and malonaldehyde.

EXAMPLE 16 TO 18

A series of three (3) reaction mixtures are subjected to 40 psi molecular oxygen at 50° C. for 1 hour. These reaction mixtures are as follows:
0.25 mmol of $(CH_3CN)_2PdCl$
0.50 mmol of CuCl
10.0 mmol of allyl acetate
5 ml of alcohol as shown below
Results of these reactions are as follows:

| Example | Alcohol | % Conversion | % Aldehyde selectivity(1) | % yield of aldehyde ketone+ |
|---|---|---|---|---|
| 16 (Comparative) | n-butanol | 97 | 26 | 20 |
| 17 | sec-butanol | 82 | 49 | 28 |
| 18 | t-butanol | 89 | 86 | 54 |

(1) moles of aldehyde over mols of aldehyde plus mols of ketone) × 100
(2) acetoxyacetone plus 3-acetoxypropionaldehyde These results indicate that aldehyde selectivity is dependent on choice of solvent with sec-butanol, and particularly t-butanol, providing higher aldehyde selectivities than the corresponding primary alcohol, n-butanol. Also, with the n-butanol (Example 16), significant ketal/acetal products are formed along with substantial exchange of the acetoxy group with butoxy. Similar results are obtained with sec-butanol (Example 17) although significantly less of the ketal/acetal products form, and such products that do form later decompose to the ketone and aldehyde compounds. In addition, in Example 17, there is less exchange of the acetoxy group for butoxy than in Example 16. In Example 18, no ketal/acetal products are observed and very little exchange of the acetoxy group for the t-butoxy group occurs. The yield of aldehyde plus ketone advantageously is increased using sec-butanol, and in particular t-butanol, relative to such yield obtained using n-butanol.

EXAMPLE 19

Example 1 is repeated except that water in an amount equal to 22 equivalents (mols) per equivalent (mol) of palladium is added. The initial oxidation rate is increased by a factor of 1.9. The initial ketone formation rate increases by a factor of 3.1 whereas the initial aldehyde formation rate increase by a factor of 1.6. The final aldehyde selectivity after three (3) hours is 31% without water and 19% with water.

Thus, depending on the desired result it may be advantageous to operate substantially or totally dry or with a small or limited concentration of water. If the olefin substrate is susceptible to being isomerized at the reaction conditions, the presence of water may be effective to inhibit such isomerization.

EXAMPLES 20 AND 21

Example 1 is repeated twice, once at 20 psi molecular oxygen and once at 80 psi molecular oxygen.

There is little dependence of the rate of 2-octanone formation on oxygen pressure between 20 psi and 40 psi, although this rate increases significantly at 80 psi. However, the rate of octonaldehyde formation seems to follow a 0.7 order dependence on oxygen pressure. Also, both rates have an apparent zero-order dependence on 1-octene concentration, which dependence is especially noticeable at 80 psi molecular oxygen.

EXAMPLES 22 TO 28

Example 14 is repeated a number of times except that each time the LiCl is replaced by a different material, as shown below.

Results of these tests (and Example 14), after 3 hours reaction time, are as follows:

| Example | salt | % conversion | % aldehyde[1] | % t-butoxyether[1] | % t-butoxyacrolein[1] |
|---|---|---|---|---|---|
| 14 | LiCl | 92 | 55 | 2.9 | 26 |
| 22 | LiBr | 81 | 51 | 1.0 | 22 |
| 23 | LiI | 0 | — | — | — |
| 24 | NaCl | 97 | 75 | 1.8 | 9.2 |
| 25 | KCl | 67 | 77 | 14 | 22 |
| 26 | CsCl | 89 | 70 | 13 | 21 |
| 27 | $MgCl_2$ | 100 | 70 | 27 | 4 |
| 28 | Quaternary chloride[2] | 98 | 76 | 0 | 0 |

[1]% Aldehyde is (mols of 3-acetoxy-and 3-t-butoxypropanal produced over (mols of 3-acetoxy-and 3-t-butoxy propanol produced plus mols of acetoxy- and t-butoxyacetone produced)) × 100; % t-butoxy ether is (mols of 3-t-butoxypropanal and t-butoxyacetone produced over (mols of 3-t-butoxypropanal and t-butoxyacetone produced plus mols of the corresponding acetates produced)) × 100; % t-butoxyacrolein is (mols of t-butoxyacrolein produced over (mols of t-butoxyacrolein plu s mols of other identified products produced)) × 100.
[2]Methyl trioctyl ammonium chloride.

The addition of lithium bromide slows the rate, but otherwise gives similar selectivities to lithium chloride. The addition of lithium iodide completely stops the reaction. Sodium chloride provides the highest activity, it is more selective toward aldehyde formation, and it produces less t-butoxy ether and t-butoxyacrolein. Potassium and cesium chloride provide slower reactions and produce more t-butoxy ethers than does lithium chloride, but have higher aldehyde selectivities. Magnesium chloride is particularly active, but gives high amounts of the t-butoxy ethers. Methyl trioctyl ammonium chloride is an excellent auxiliary salt because it produces virtually no t-butoxy ethers or t-butoxyacrolein, but provides high selectivity for aldehyde.

EXAMPLE 29

An oxidation reaction using allyl acetate as the substrate is conducted as follows. A mixture of 0.25 mmol of $(CH_3CN)_2PdCl_2$, 0.5 mmol of CuCl, 0.5 mmol of NaCl and 5 ml of t-butyl alcohol is pretreated by stirring at room temperature for one (1) hour. 10 mmol of allyl acetate is then added and the combined mixture is heated under molecular oxygen. Reaction conditions include a temperature of 60° C., for three (3) hours at 40 psi molecular oxygen. Results of this test are presented in the Summary Table below.

EXAMPLES 30 TO 41

Example 29 is repeated twelve (12) times, with alterations as indicated below. Results of these tests are presented in the Summary Table below.

In Example 30, the mixture includes four (4) equivalents of t-butyl nitrite per equivalent of Pd.

In Example 31, the mixture includes 40 equivalents of t-butyl nitrite per equivalent of Pd.

In Example 32, the mixture includes four (4) equivalents of t-butyl nitrite per equivalent of Pd, and no CuCl.

In Example 33, the mixture includes 40 equivalents of t-butyl nitrite, per equivalent of Pd, and no CuCl.

In Example 34, the mixture includes four (4) equivalents of t-butyl nitrite per equivalent of Pd, no CuCl and no NaCl.

In Example 35, Example 34 is repeated except that Pd(OAc)$_2$ is used in place of $(CH_3CN)_2PdCl_2$.

In Example 36, Example 34 is repeated except that Pd$(O_2CCF_3)_2$ was used in place of $(CH_3CN)_2PdCl_2$.

In Example 37, Example 34 is repeated except that Pd(acac)$_2$, palladium acetylacetonate, is used in place of $(CH_3CN)_2PdCl_2$.

In Example 38, Example 34 is repeated except that sodium nitrite is used in place of t-butyl nitrite.

In Example 39, Example 34 is repeated except the mixture includes 4 equivalents of t-butyl nitrite per equivalent of Pd, 5 mmols of $CuCl_2$, and the $(CH_3CN)_2PdCl_2$ is replaced by palladium metal deposited on carbon particles (10% Pd on carbon, 0.24 mmol Pd).

In Example 40, Example 34 is repeated except that the reaction takes place under 40 psi of nitrogen (and no molecular oxygen).

In Example 41, Example 40 is repeated except that the mixture includes 40 equivalents of t-butyl nitrite per equivalent of Pd.

SUMMARY TABLE I

| Example | % conv. | aldehyde selectivity[1] 3 hours | 5 hour | yield, wt %[2] Isomeric acetates[3] | butyl ether[4] | acetic acid | ketone + aldehyde[5] |
|---|---|---|---|---|---|---|---|
| 29 | 99.81% | 77.52% | 68.59% | 4.1% | 2.58% | 29.69% | 53.00% |
| 30 | 99.89% | 72.44% | 70.52% | 0.11% | 0.81% | 14.56% | 80.98% |
| 31 | 99.68% | 65.30% | 51.42% | 0.11% | 0.86% | 28.06% | 57.68% |
| 32 | 88.88% | 72.13% | 70.70% | 5.51% | 1.53% | 23.95% | 53.45% |
| 33 | 95.79% | 65.48% | 52.21% | 0.43% | 0.86% | 36.90% | 48.12% |
| 34 | 85.34% | 76.53% | 74.73% | 2.28% | 1.83% | 23.18% | 58.15% |
| 35 | 14.23% | 43.13% | 40.99% | 0.54% | 2.98% | 10.90% | 2.68% |
| 36 | 17.76% | 56.37% | 54.52% | 1.71% | 7.30% | 2.68% | 3.14% |
| 37 | 3.72% | — | — | 0.86% | — | 0.00% | 0.00% |
| 38 | 25.91% | 59.88% | 56.88% | 5.15% | 7.03% | 6.27% | 5.46% |
| 39 | 71.18% | 61.69% | 27.26% | 0.54% | 1.04% | 12.68% | 39.35% |
| 40 | 14.95% | 81.45% | 79.56% | 0.22% | 16.54% | 6.36% | 1.74% |

SUMMARY TABLE I-continued

| | | aldehyde selectivity[1] | | yield, wt %[2] | | | |
|---|---|---|---|---|---|---|---|
| Example | % conv. | 3 hours | 5 hour | Isomeric acetates[3] | butyl ether[4] | acetic acid | ketone + aldehyde[5] |
| 41 | 22.18% | 54.86% | 52.83% | 0.54% | 5.34% | 2.52% | 7.34% |

[1](mols of aldehyde over mols of aldehyde plus mols of ketone) × 100
[2]Based on allyl acetate charged
[3]E- and Z-propenyl acetates
[4]t-butoxyacetone plus 3-t-butoxypropanal
[5]acetoxyacetone plus 3-acetoxypropionaldehyde These results indicate that with both CuCl and four (4) equivalents of t-butyl nitrite (Example 30) a very high yield of ketone plus aldehyde is obtained. This reaction produces little acetic acid, little allyl acetate isomerization and little t-butyl ethers. However, with 40 equivalents of t-butyl nitrite present (Example 31), the oxidation is slower, with significant decomposition of the acetoxypropionaldehyde. These trends also occur in experiments (e.g., Examples 32 and 33) without CuCl.

Using Pd(OAc)$_2$, Pd(O$_2$CCF$_3$)$_2$ or Pd(acac)$_2$, without copper or chloride (Examples 35, 36 and 37), much less oxidation activity was achieved. Using sodium nitrite instead of t-butyl nitrite (Example 38) results in little activity. Example 39 indicates that supported palladium in the presence of CuCl provides useful activity. It should be noted that after this reaction with the supported palladium, the solution contained 214 ppm by weight of palladium. Example 40 and 41 demonstrate that molecular oxygen is advantageously present in order to obtain suitable or acceptable conversions, and that alkyl nitrites provide increased conversion and increased yield of ketone plus aldehyde.

EXAMPLE 42

An oxidation reaction using allyl acetate as the substrate is conducted as follows. A mixture of 0.25 mmol of PdCl$_2$, 0.5 mmol of CuCl, 0.5 mmol of NaCl, 42 mg of water and 1 ml of t-butyl alcohol is stirred overnight in air before adding another 4 ml of t-butyl alcohol and 10 mmol of allyl acetate. Reaction conditions include a temperature of 60° C. for three (3) hours at 40 psi molecular oxygen. Results of this test are presented in the Summary Table II below.

EXAMPLES 43 TO 78

Example 42 is repeated a number of times. In each repetition, the mixture includes four (4) equivalents or mols of —C≡N groups (per equivalent or mol of Pd) of a different nitrile component, as indicated in the Summary Table II below. In Examples 74 to 78, the mixture includes 32 equivalents (per equivalent of Pd) of a different nitrile component, as indicated in the Summary Table II below. Results of these tests are presented in the Summary Table II below.

SUMMARY TABLE II

| Example | nitrile component | % conv. | aldehyde selectivity[1] | | yield, wt %[2] | | | |
|---|---|---|---|---|---|---|---|---|
| | | | 3 hours | 5 hours | Isomeric acetates[3] | butyl ether[4] | acetic acid | ketone + aldehyde[5] |
| 42 | control-no nitrile | 99.79% | 71.98% | 68.99% | 0.10% | 0.67% | 43.72% | 58.43% |
| 43 | 4-nitrobenzonitrile | 100.00% | 71.16% | 69.35% | 0.71% | -0.31% | 29.51% | 75.08% |
| 44 | 5-oxohexanenitrile | 99.80% | 70.14% | 68.37% | 0.51% | 1.53% | 22.94% | 75.03% |
| 45 | pentafluorobenzonitrile | 99.70% | 70.59% | 68.65% | 0.50% | 0.67% | 23.73% | 69.55% |
| 46 | isophorone nitrile | 100.00% | 73.97% | 72.03% | 0.00% | 3.63% | 27.61% | 65.50% |
| 47 | pivalonitrile | 100.00% | 73.14% | 70.66% | 0.00% | 5.10% | 36.84% | 65.29% |
| 48 | benzonitrile | 100.00% | 65.67% | 62.22% | 0.00% | 0.37% | 40.58% | 62.61% |
| 49 | 4-fluorobenzonitrile | 100.00% | 74.40% | 71.69% | 0.00% | 5.64% | 39.79% | 61.73% |
| 50 | Fluoroacetonitrile | 100.00% | 75.03% | 73.19% | 0.00% | 2.98% | 29.21% | 60.78% |
| 51 | octyl cyanide | 100.00% | 70.33% | 68.05% | 0.00% | 2.55% | 35.27% | 59.72% |
| 52 | acetonitrile | 100.00% | 72.55% | 70.32% | 0.00% | 3.73% | 31.01% | 59.50% |
| 53 | 4-acetylbenzonitrile | 100.00% | 67.35% | 64.88% | 1.62% | 0.67% | 29.82% | 57.94% |
| 54 | isobutyronitrile ligand | 100.00% | 72.20% | 69.99% | 0.00% | 3.79% | 35.09% | 57.04% |
| 55 | 2,5-dimethylbenzonitrile | 100.00% | 72.81% | 70.78% | 0.20% | 3.66% | 35.08% | 53.26% |
| 56 | polyacrylonitrile (10 eq) | 99.90% | 72.14% | 69.17% | 0.21% | 5.90% | 40.37% | 52.03% |
| 57 | 2,6-difluorobenzonitrile | 100.00% | 73.89% | 71.07% | 0.00% | 6.86% | 35.29% | 51.67% |
| 58 | HMHN[6] | 99.90% | 64.73% | 62.88% | 0.40% | 0.30% | 32.86% | 52.03% |
| 59 | 4-methylbenzonitrile | 89.05% | 62.61% | 59.05% | 32.45% | 0.00% | 18.43% | 38.83% |
| 60 | 4-dimethylamino-benzonitrile | 83.81% | 58.04% | 56.13% | 32.08% | 0.00% | 14.01% | 29.32% |
| 61 | 4-methoxybenzonitrile | 73.80% | 59.34% | 55.96% | 40.95% | 0.00% | 7.97% | 20.70% |
| 62 | 2,6-dimethoxybenzonitrile | 60.95% | 46.72% | 44.51% | 33.11% | 0.00% | 5.98% | 12.11% |
| 63 | acrylonitrile | 0.00% | 0.00% | 0.00% | 0.00% | 0.00% | 4.05% | 0.00% |
| 64 | dimethylaminoacetonitrile | 0.00% | — | — | 0.10% | — | 0.00% | 0.00% |
| 65 | 3-dimethylaminopropionitrile | 0.00% | — | — | 0.20% | — | 0.00% | 0.00% |
| 66 | 1,2-dicyanoethane | 96.71% | 62.17% | 59.20% | 18.83% | 0.00% | 25.75% | 45.19% |
| 67 | 1,3-dicyanopropane | 0.00% | 56.25% | 53.57% | 1.59% | 0.00% | 0.00% | 1.37% |
| 68 | 1,4-dicyanobutane | 60.87% | 54.55% | 52.87% | 40.66% | 0.00% | 7.65% | 12.56% |
| 69 | 1,5-dicyanopentene | 96.97% | 54.14% | 49.52% | 20.44% | 0.47% | 33.05% | 32.87% |
| 70 | 1,4-dicyanobenzene | 73.63% | 54.55% | 52.58% | 25.85% | 0.00% | 16.79% | 19.69% |
| 71 | TONQ[7] | 89.84% | 69.65% | 68.15% | 4.78% | 2.08% | 23.56% | 47.77% |
| 72 | tetracyanoethylene | 85.60% | 68.84% | 65.62% | 0.30% | 13.84% | 27.55% | 45.63% |
| 73 | K$_4$Fe(CN)$_6$ 3H$_2$O | 0.00% | 0.00% | 0.00% | 10.70% | — | 0.51% | 0.00% |
| 74 | 5-oxohexanenitrile | 95.63% | 62.92% | 60.67% | 4.67% | 0.17% | 12.88% | 89.38% |
| 75 | HMHN[6] | 98.67% | 64.62% | 62.04% | 1.44% | 0.28% | 14.21% | 83.05% |
| 76 | acetonitrile | 99.80% | 69.84% | 67.78% | 0.71% | 1.43% | 28.61% | 69.87% |

SUMMARY TABLE II-continued

| Example | nitrile component | % conv. | aldehyde selectivity[1] 3 hours | aldehyde selectivity[1] 5 hours | yield, wt %[2] Isomeric acetates[3] | yield, wt %[2] butyl ether[4] | yield, wt %[2] acetic acid | yield, wt %[2] ketone + aldehyde[5] |
|---|---|---|---|---|---|---|---|---|
| 77 | pentafluorobenzonitrile | 99.80% | 61.13% | 58.07% | 6.48% | 0.28% | 37.66% | 54.84% |
| 78 | p-nitrobenzonitrile | 99.08% | 48.03% | 42.77% | 0.72% | 0.48% | 40.99% | 32.95% |

[1](mols of aldehyde over mols of aldehyde plus mols of ketone) × 100
[2]Based on allyl acetate charged
[3]E-and Z-propenyl acetates
[4]t-butoxyacetone plus 3-t-butoxypropanol
[5]acetoxyacetone plus 3-acetoxypropionaldehyde
[6]HMHN = 5-hydroxy-5-methylhexanenitrile
[7]TCNQ = Tetracyanoquinodimethane The addition of acetonitrile to the reaction mixture tends to (1) reduce precipitation of palladium metal and (2) reduce the amount of allyl exchange with the alcohol solvent in the case of allyl acetate. In general, nitriles with electron withdrawing substituents provide higher yields of oxidized products. Nitriles with electron donating substituents tend to slow the oxidation reaction and reduce the total yield. Certain nitriles act as poisons. Higher concentrations of certain nitrile components increase the total yield, but tend to reduce the aldehyde-to ketone ratio.

EXAMPLES 79 to 82

Four (4) oxidation reactions are conducted. In each, a mixture containing 0.25 mmol of $(CH_3CN)_2PdCl_2$, 0.5 mmol of CuCl, 0.5 mmol of NaCl and 5 ml of t-butyl alcohol is prepared.

In Example 79, the mixture is stirred for 30 minutes at 60° C. under 40 psi of molecular oxygen. In Examples 80 to 82, the mixture is stirred for 1 hour at room temperature under 1 atmosphere of air. In Example 82, the source of the $(CH_3CN)_2 PdCl_2$ is different than the source of this material which is used in Examples 79 to 81. In Example 81, the mixture contains 0.7% by weight of water. In Example 82, the mixture includes 2 equivalents of $CH_3CN$ per equivalent of Pd.

In each case, after the pretreatment 10 mmol of allyl acetate is added to the mixture and the reaction is conducted for 3 hours, at 60° C. under 40 psi of molecular oxygen.

Results of these tests are as follows:

| Example | % conv. | Aldehyde selectivity[1] | yield, wt %[2] Isomeric acetates[3] | yield, wt %[2] butyl ether[4] | yield, wt %[2] Acetic Acid | yield, wt %[2] Ketone + Aldehyde[5] |
|---|---|---|---|---|---|---|
| 79 | 95.39% | 75.39% | 14.4% | 1.81% | 43.88% | 57.0% |
| 80 | 99.81% | 77.52% | 4.14% | 2.58% | 29.69% | 53.7% |
| 81 | 100% | 73.59% | 0.29% | 7.07% | 29.80% | 46.2% |
| 82 | 100% | 82.60% | 6.44% | 0.00% | 14.33% | 55.6% |

[1](mols of aldehyde over mols of aldehyde plus mols of ketone) × 100
[2]Based on allyl acetate charged
[3]E-and Z-propenyl acetates
[4]t-butoxyacetone plus 3-t-butoxypropanol
[5]acetoxyacetone plus 3-acetoxypropionaldehyde The pretreatment in Example 80 results in reduced olefin isomerization using allyl acetate as the substrate relative to the pretreatment in Example 79. Comparing Examples 81 and 80, the presence of a limited amount of water is shown to reduce or inhibit olefin isomerization. Also, comparing Example 82 and 80, the presence of acetonitrile provides reduced yields of acetic acid and butyl ether. The pretreatment in Example 82 differs from the pretreatment used in Example 52 so that the differences in the results obtained in these two examples indicates that the pretreatment used does influence the effect of other process variables, such as the effect of the presence of acetonitrile.

EXAMPLES 83 and 84

Example 80 is repeated twice except that the mixture contains 0.1 mmol of $(CH_3CN)_2PdCl_2$, 0.7% by weight of water and 2 equivalents of $CH_3CN$ per equivalent of Pd. The reactions are conducted under 80 psi molecular oxygen.

In Example 83, the allyl acetate is added to the mixture at reaction conditions over a two (2) hour period. In Example 84, all the ally acetate is added at one time at the start of the reaction period.

Results of these tests are as follows:

| Example | % conv. | Aldehyde selectivity[1] | yield, wt %[2] Isomeric acetates[3] | yield, wt %[2] butyl ether[4] | yield, wt %[2] Acetic Acid | yield, wt %[2] Ketone + Aldehyde[5] |
|---|---|---|---|---|---|---|
| 83 | 100% | 70.51% | 1.45% | 0.58% | 19.35% | 88.35% |
| 84 | 94.56% | 68.49% | 29.37% | 0.00% | 45.18% | 32.30% |

[1](mols of aldehyde over mols of aldehyde plus mols of ketone) × 100
[2]Based on allyl acetate charged
[3]E-and Z-propenyl acetates
[4]t-butoxyacetone plus 3-t-butoxypropanol
[5]acetoxyacetone plus 3-acetoxypropionaldehyde These results indicate that slow addition of allyl acetate, as opposed to batch addition, greatly increases the yield of useful products.

While this invention has been described with respect to various specific examples and embodiments, it is to be

I claim:

1. A process for the oxidation of a compound having a terminal carbon-carbon double bond to produce the corresponding aldehyde comprising contacting said compound with molecular oxygen in the presence of a Group VIII metal component, initially free of NO ligands and NO₂ ligands, in an amount effective to promote the oxidation of said compound, a reoxidation compound in an amount effective to reoxidize a reduced Group VIII metal component to said Group VIII metal component and at least one alcohol selected from the group consisting of secondary alcohols, tertiary alcohols and mixtures thereof in an amount effective to increase the aldehyde selectivity of said oxidation relative to conducting said contacting in the presence of a corresponding primary alcohol in place of said at least one alcohol, said contacting occurring at conditions effective to oxidize said compound and form said corresponding aldehyde.

2. The process of claim 1 wherein said alcohol is a tertiary alcohol and mixtures thereof.

3. The process of claim 2 wherein said alcohol is tertiary butyl alcohol.

4. The process of claim 1 wherein said compound contains 2 to about 30 carbon atoms per molecule.

5. The process of claim 1 wherein said Group VIII metal component comprises a Group VIII metal complex.

6. The process of claim 1 wherein said Group VIII metal component comprises a palladium-containing component.

7. The process of claim 1 wherein said contacting occurs in the presence of a nitrile component.

8. The process of claim 7 wherein said nitrile component is selected from the group consisting of acetonitrile, benzonitrile, para nitro benzonitrile, 5-oxohexanenitrile and mixtures thereof.

9. The process of claim 6 wherein said Group VIII metal component comprises $(CH_3CN)_2PdCl_2$.

10. The process of claim 1 wherein said reoxidation component comprises a component of a metal which is a redox active at said conditions.

11. The process of claim 1 wherein said reoxidation component comprises an organic component which is redox active at said conditions.

12. The process of claim 11 wherein said organic component includes at least one —ONO group.

13. The process of claim 11 wherein said organic component comprises (CH₃)₃C—ONO 14. The process of claim 1 wherein said contacting further takes place in the presence of at least one organic component including at least one —ONO group which is reducible at said conditions in an amount effective to facilitate the oxidation of said compound.

15. The process of claim 14 wherein said organic component is selected from the group consisting of compounds having the following formula:

R(—ONO)ₐ and mixtures thereof, wherein R is selected from the group consisting of hydrocarbyl radicals and substituted hydrocarbyl radicals and a is an integer in the range of 1 to about 10.

16. The process of claim 15 wherein R is alkyl and contains 1 to about 10 carbon atoms and a is 1.

17. The process of claim 14 wherein said organic component comprises (CH₃)₃C—ONO 18. The process of claim 1 wherein said contacting takes place in the presence of monovalent copper in an amount effective to increase the yield of said aldehyde and the corresponding ketone from said oxidation.

19. The process of claim 1 wherein said contacting occurs in the presence of a chloride component in an amount effective to enhance at least one of the rate of said oxidation and the aldehyde selectivity of said oxidation.

20. The process of claim 19 wherein said chloride component is selected from the group consisting of LiCl, NaCl, quaternary ammonium chlorides and mixtures thereof.

21. The process of claim 1 wherein said contacting occurs in the presence of an inhibitor component in an amount effective to inhibit the isomerization of said compound at said conditions.

22. The process of claim 21 wherein said inhibitor component comprises a divalent copper component.

23. The process of claim 1 wherein said contacting occurs in the substantial absence of water.

24. The process of claim 1 wherein said contacting occurs in the presence of water in an amount effective to do at least one of the following: increase the rate of said oxidation; and inhibit the isomerization of said compound at said conditions.

25. A process for the oxidation of a compound having a terminal carbon-carbon double bond to produce the corresponding aldehyde comprising contacting said compound with molecular oxygen in the presence of a Group VIII metal component initially free of NO ligands and NO₂ ligands in an amount effective to promote the oxidation of said compound, a copper component in an amount effective to facilitate the oxidation of said compound and at least one alcohol selected from the group consisting of secondary alcohols, tertiary alcohols and mixtures thereof in an amount effective to increase the aldehyde selectivity of said oxidation relative to conducting said contacting in the presence of a corresponding primary alcohol in place of said at least one alcohol, said contacting occurring at conditions effective to oxidize said compound and form said corresponding aldehyde.

26. The process of claim 25 wherein said alcohol is a tertiary alcohol and mixtures thereof.

27. The process of claim 25 wherein said alcohol is tertiary butyl alcohol.

28. The process of claim 25 wherein said Group VIII metal component comprises a Group VIII metal complex.

29. The process of claim 28 wherein said Group VIII metal component comprises a palladium-containing component.

30. The process of claim 29 wherein said contacting occurs in the presence of a nitrile component.

31. The process of claim 29 wherein said copper component comprises at least one copper halide.

32. The process of claim 25 wherein said contacting further takes place in the presence of at least one organic component including at least one —ONO group which is reducible at said conditions in an amount effective to facilitate the oxidation of said compound.

33. The process of claim 32 wherein said organic component is selected from the group consisting of compounds having the following formula:

R(—ONO)a and mixtures thereof, wherein R is selected from the group consisting of hydrocarbyl radicals and substituted hydrocarbyl radicals and a is an integer in the range of 1 to about 10.

34. The process of claim 33 wherein R is alkyl and contains 1 to about 10 carbon atoms and a is 1.

35. The process of claim 32 wherein said organic component comprises (CH$_3$)$_3$C—ONO 36. The process of claim 25 wherein said contacting occurs in the presence of a chloride component in an amount effective to enhance at least one of the rate of said oxidation and the aldehyde selectivity of said oxidation.

37. The process of claim 25 wherein said contacting occurs in the presence of an inhibitor component in an amount effective to inhibit the isomerization of said compound at said conditions.

38. The process of claim 25 wherein said contacting occurs in the substantial absence of water.

39. The process of claim 31 wherein the copper halide is CuCl.

40. The process of claim 31 wherein said copper halide is CuCl$_2$.

41. The process of claim 31 wherein said copper halide is CuCl and CuCl$_2$.

42. The process of claim 1 wherein the reoxidation component is a divalent copper component and a monovalent copper component wherein the monovalent copper component is generated in situ by a monovalent copper yielding component.

43. The process of claim 42 wherein said monovalent copper yielding component is selected from the group consisting of basic components, copper reducing components and mixtures thereof.

44. The process of claim 42 wherein said monovalent copper yielding component is selected from the group consisting of alkali metal hydroxides, alkaline earth metal hydroxides, metal hydrides, elemental metals, organic copper reducing components and mixtures thereof.

45. The process of claim 42 wherein said monovalent copper yielding component is selected from the group consisting of lithium hydroxide, NaBH$_4$, 2,6-di-t-butyl-p-cresol and mixtures thereof.

* * * * *